US007914893B2

(12) United States Patent
Handrosch et al.

(10) Patent No.: US 7,914,893 B2
(45) Date of Patent: *Mar. 29, 2011

(54) PARTICLES COMPRISING AN ANION-BINDING LAYER CONTAINING ANION-FORMING ORGANIC ACTIVE COMPOUNDS, AND METHOD OF MAKING AND USING THEREOF

(75) Inventors: Carsten Handrosch, Muehltal (DE); Thomas Rudolph, Darmstadt (DE); Herwig Buchholz, Frankfurt (DE); Soheila Anzali, Seeheim-Jugenheim (DE)

(73) Assignee: Merck Patent GmbH, Darmstadt (DE)

( * ) Notice: Subject to any disclaimer, the term of this patent is extended or adjusted under 35 U.S.C. 154(b) by 594 days.

This patent is subject to a terminal disclaimer.

(21) Appl. No.: 11/802,715

(22) Filed: May 24, 2007

(65) Prior Publication Data

US 2007/0275244 A1 Nov. 29, 2007

(30) Foreign Application Priority Data

May 24, 2006 (DE) .................. 10 2006 024 289

(51) Int. Cl.
*B32B 5/16* (2006.01)
*B05D 7/00* (2006.01)
*C09C 1/00* (2006.01)
*C09C 1/44* (2006.01)

(52) U.S. Cl. ........ 428/403; 106/415; 106/472; 106/474; 106/482; 427/212; 427/215; 427/218; 428/379; 428/389; 428/401

(58) Field of Classification Search .................. 428/403, 428/407, 379, 39, 401; 427/212, 215, 218; 106/415, 472, 474, 482
See application file for complete search history.

(56) References Cited

U.S. PATENT DOCUMENTS

| | | | | |
|---|---|---|---|---|
| 4,063,000 A | * | 12/1977 | Aonuma et al. | 428/403 |
| 5,641,813 A | * | 6/1997 | Franklin et al. | 514/721 |
| 5,786,381 A | * | 7/1998 | Franklin et al. | 514/557 |
| 6,837,925 B2 | * | 1/2005 | Kubo et al. | 106/486 |
| 7,288,318 B2 | * | 10/2007 | Choy et al. | 428/402 |
| 7,799,126 B2 | * | 9/2010 | Handrosch et al. | 106/482 |
| 2003/0163877 A1 | * | 9/2003 | Baker et al. | 8/405 |
| 2005/0112074 A1 | * | 5/2005 | Arai et al. | 424/70.1 |
| 2006/0225609 A1 | * | 10/2006 | Rueger et al. | 106/31.9 |

* cited by examiner

*Primary Examiner* — H. (Holly) T Le
(74) *Attorney, Agent, or Firm* — Millen, White, Zelano & Branigan, P.C.

(57) ABSTRACT

Disclosed are particles containing substrates and an anion-binding layer, containing one or more anion-forming organic active compounds or active compound/colorant mixtures; processes for preparing said particles and to methods of use thereof in cosmetics, pharmaceuticals, formulations, paints, coatings, plastics, films, in security printing, in security features in documents or identity papers, for coloring seed, for coloring foods or in medicament coatings and for the preparation of pigment compositions and dry preparations.

23 Claims, No Drawings

PARTICLES COMPRISING AN ANION-BINDING LAYER CONTAINING ANION-FORMING ORGANIC ACTIVE COMPOUNDS, AND METHOD OF MAKING AND USING THEREOF

The present invention relates to particles comprising substrates and an anion-binding layer, wherein the anion-binding layer comprises one or more anion-forming organic active compounds. The present invention furthermore relates to processes for the production of particles and to the use thereof in cosmetics, pharmaceuticals, formulations, paints, coatings, plastics, films, in security printing, in security features in documents and identity papers, for colouring seed, for colouring foods or in medicament coatings and for the preparation of pigment compositions and dry preparations.

Active compounds play an eminent role in cosmetics and in pharmaceutical products. Examples of cosmetic active compounds are UV filters, inflammation-inhibiting substances, etc. In general, the said active compounds are organic functional active compounds. These organic functional active compounds are usually applied or administered in the form of a formulation.

Examples of such formulations in cosmetics are, for example, creams, ointments or gels, in the case of pharmaceutical active compounds for example tablets, dragees, solutions, but also ointments.

However, the said active compounds are frequently not sufficiently stable in the formulations or can react with other constituents of the formulation. Furthermore, the dosage of the active compounds on use of the formulations frequently cannot be controlled, for example the skin comes into contact with the entire concentration of the active compound in the case of application of an ointment, even if this was initially undesired. There are a number of approaches to improving or regulating the release or stabilisation of active compounds. This is in many cases carried out by encapsulating the active compounds in carriers, which are then intended to release the active compounds in a specific manner.

The object of the present invention is therefore to provide particles which are capable of stabilising active compounds and/or releasing them in a controlled manner. The object of the present invention is furthermore to achieve synergistic action profiles through a suitable choice of substrate and anion-binding layer.

Surprisingly, the above-mentioned object is achieved by particles of the present invention.

Accordingly, the present invention relates firstly to particles comprising substrates and an anion-binding layer which comprises one or more anion-forming organic active compounds, also referred to as the fixing layer.

The particles according to the invention can achieve two fundamentally different functions in relation to the bound anionic active compound: at low pH (<6), the fixing layer dissolves successively, giving rise to a controlled-release function of the particles. At higher pH (>6), by contrast, the fixing layer is stable and thus exerts a protective and stabilising function on the bound anionic active compound. The particles in accordance with the present invention are thus, in particular, multifunctional hybrid particles.

Owing to the advantageous properties, the particles according to the invention are universally suitable for a large number of widely differing applications. The present invention accordingly also relates to the use of these particles in cosmetics, pharmaceuticals, formulations, paints, coatings, plastics, films, in security printing, in security features in documents and identity papers, for colouring seed, for colouring foods or in medicament coatings and for the preparation of pigment compositions and dry preparations.

The particles according to the invention are based on substrates, which can basically have any shape. Examples of appropriately shaped substrates are flake-form, spherical or needle-shaped substrates, but it is also possible to employ irregularly shaped substrates. For the purposes of the present invention, spherical is taken to mean ball-shaped, but also asymmetrically ball-shaped, for example elliptical.

Suitable flake-form substrates are, for example, glass flakes, $SiO_2$ flakes, $Al_2O_3$ flakes, BiOCl flakes, graphite flakes, synthetic or natural flake-form iron oxide or flake-form metals. Suitable metal flakes can contain, inter alia, aluminium, titanium, bronze, steel or silver, preferably aluminium and/or titanium. The metal flakes here may have been passivated by appropriate treatment.

The size of the flake-form base substrates is not crucial per se and can be matched to the particular application. The diameter of the flake-form substrates is on average usually between 1 and 500 µm, preferably between 5 and 200 µm and in particular 10-200 µm. Preferred smaller particle sizes are furthermore those in the range from 1 to 100 µm, in particular 5-60 µm and 1-15 µm. Their average thickness is between 0.05 and 10 µm and preferably 0.1 to 1.0 µm. The average aspect ratio of the flake-form substrates, i.e. the ratio of the average length measurement value, which here corresponds to the average diameter, to the average thickness measurement value, is usually 5 to 750, preferably 10 to 300 and particularly preferably 20 to 200.

Flake-form substrates are preferably glass flakes, $SiO_2$ flakes or $Al_2O_3$ flakes and, owing to their particularly smooth surface and very high reflection capacity, very particularly preferably glass flakes.

The $SiO_2$ flakes preferably employed are synthetic $SiO_2$ flakes which have a uniform layer thickness and are preferably produced in accordance with International Application WO 93/08237 on a continuous belt by solidification and hydrolysis of a water-glass solution. Uniform layer thickness here is taken to mean a layer-thickness tolerance of 3 to 10%, preferably 3 to 5%, of the total dry layer thickness of the particles. The flake-form silicon dioxide particles are generally in amorphous form. Synthetic flakes of this type have the advantage over natural materials, such as, for example, mica, that the layer thickness can be adjusted with regard to the desired effects and the layer-thickness tolerance is limited.

In principle, all glass types and forms known to the person skilled in the art (for example flakes, beads, fibres, etc.) can be used for the particles according to the invention. Very particular preference is given to glass flakes, which can consist of all glass types known to the person skilled in the art, in particular Ca-Al-borosilicate glasses, such as, for example, window glass, C glass, E glass, ECR glass, Duran® glass, laboratory equipment glass or optical glass. Particular preference is given to E glass or ECR glass, but also iron-, bismuth-, niobium-, tin- and/or titanium-containing glasses. The refractive index of the flakes is preferably 1.20-2.20, in particular 1.50-1.70.

Suitable flake-form substrates are accordingly substrates based on Ca-Al-borosilicate (for example RONASTAR® from Merck KGaA), $SiO_2$ (for example COLORSTREAM® from Merck KGaA), $Al_2O_3$ (for example XIRALLIC® from Merck KGaA), natural leaf-shaped iron oxide (for example MIOX® from Kärntner Montan Industrie), synthetic or natural graphite, synthetic leaf-shaped iron oxide (for example TAROX® from Titan Kogyo), or metallic aluminium.

Spherical substrates are based, in particular, on Ca-Al-borosilicate, $SiO_2$, $TiO_2$, $Al_2O_3$, $GeO_2$, $ZrO_2$, ZnO, $B_2O_3$, Ga$_2$O$_3$, In$_2$O$_3$, SnO$_2$, but also on (Ca/Mg)$_2$(OH)(PO$_4$), kaolin, BaSO$_4$, chalk, MgCO$_3$, BiOCl (for example Biron® ESQ). Suitable substrates are furthermore also spherical coloured pigments, such as, for example, natural or synthetic iron oxide, ultramarine blue, carbon black, chromium oxide green, cobalt blue, Berlin Blue and manganese violet. In particular, spherical substrates of ZnO or TiO$_2$ act as UV filters. Particles based on these substrates are particularly suitable for the production of multifunctional particles. The substrate exhibits a functional action here, which is supplemented by the active compounds bound in the anion-binding layer and their action.

Spherical capsules of the above-mentioned materials which encapsulate organic and/or inorganic compounds and materials are likewise suitable as spherical substrates. The encapsulated compound can be selected, for example, from the group of the UV filters. Preferred capsules have capsule walls as obtained, for example, by a process described in WO 000/09652, WO 00/72806 and WO 00/71084. The capsule walls are preferably sheaths based on SiO$_2$ or TiO$_2$. An example of capsules of this type are the Eusolex® UV-Pearls™ (Merck KGaA, Darmstadt).

Particles based on spherical substrates are particularly advantageous for cosmetic and pharmaceutical applications. Depending on the material, spherical particles of the present invention exhibit good wrinkle-hiding effects, a good skin feel and can be employed both as filler and also as active agent. Furthermore, the sheen of the skin is reduced and the skin is given a softer appearance. The rolling and gliding effect of the spherical particles significantly improves the skin feel.

The size of the spherical base substrates is likewise not crucial per se and can be matched to the particular application. The diameter of the spherical particles is usually between 1 nm and 2000 μm, preferably between 5 nm and 1000 μm and particularly preferably between 10 nm and 500 μm. Spherical metal oxides, in particular metal oxides having a UV-filtering activity, preferably have an average diameter of 5 to 1000 μm, in particular 8 to 500 nm and very particularly preferably 8 to 300 nm.

In addition, needle-shaped substrates are also suitable for the purposes of the present invention. Examples thereof are glass fibres, plastic fibres and pigments having a needle-shaped crystal structure, such as, for example, yellow iron oxide (goethite).

The above-mentioned substrates may also be in the form of mixtures (for example binary or ternary mixtures), i.e., for example, flake-form substrate particles are mixed with spherical and/or needle-shaped substrate particles. The mixing ratio between spherical and non-spherical particles, for example between flake-form and needle-shaped particles, is not crucial and can be matched to the application; it can be selected, for example, between 1:99 and 99:1 parts by weight, in particular between 10:90 and 90:10 parts by weight and especially between 1:9 and 9:1 parts by weight. Mixtures of this type enable certain physical properties, such as, for example, the lustre, the hiding power or the skin feel of the end product, to be set in a specific manner.

The above-mentioned substrates may be doped with ions or elements which result in coloration of the substrate. In addition, the substrates may also be doped with ions or elements which, in addition to/besides the colour, cause a certain physical property of the substrate, for example conductivity, increased refractive index, fluorescence, phosphorescence, magnetism, NLO properties, IR or UV reflection/absorption, etc. The physical properties mentioned which are induced by ion or element doping are only intended to explain the present invention without limiting it.

In a further embodiment of the present invention, one or more transparent, semitransparent and/or opaque layers of metal oxides, metal oxide hydrates, metal suboxides, metals, metal fluorides, metal nitrides, metal oxynitrides or mixtures of these materials may be applied to the above-mentioned substrates and beneath the anion-binding layer. The metal oxide, metal oxide hydrate, metal suboxide, metal, metal fluoride, metal nitride or metal oxynitride layers or the mixtures thereof may have a low refractive index (refractive index <1.8) or a high refractive index (refractive index ≧1.8). Suitable metal oxides and metal oxide hydrates are all metal oxides and metal oxide hydrates known to the person skilled in the art, such as, for example, aluminium oxide, aluminium oxide hydrate, silicon oxide, silicon oxide hydrate, iron oxide, tin oxide, cerium oxide, zinc oxide, zirconium oxide, chromium oxide, titanium oxide, in particular titanium dioxide, titanium oxide hydrate and mixtures thereof, such as, for example, ilmenite or pseudobrookite. Metal suboxides which can be employed are, for example, the titanium suboxides. Suitable metals are, for example, chromium, aluminium, nickel, silver, gold, titanium, copper or alloys, and a suitable metal fluoride is, for example, magnesium fluoride. Metal nitrides or metal oxynitrides which can be employed are, for example, the nitrides or oxynitrides of the metals titanium, zirconium and/or tantalum. Metal oxide, metal, metal fluoride and/or metal oxide hydrate layers and very particularly preferably metal oxide and/or metal oxide hydrate layers are preferably applied to the support. Furthermore, multilayered structures comprising high- and low-refractive-index metal oxide, metal oxide hydrate, metal or metal fluoride layers may also be present, where high- and low-refractive-index layers preferably alternate. Particular preference is given to layer packages comprising a high-refractive-index layer and a low-refractive-index layer, wherein one or more of these layer packages may be applied to the support. The sequence of the high- and low-refractive-index layers here can be matched to the substrate in order to include the substrate in the multilayered structure. In a further embodiment, the metal oxide, metal oxide hydrate, metal suboxide, metal, metal fluoride, metal nitride or metal oxynitride layers may be mixed or doped with colorants or other elements. Suitable colorants or other elements are, for example, organic or inorganic coloured pigments, such as coloured metal oxides, for example magnetite, chromium oxide or coloured pigments such as, for example, Berlin Blue, ultramarine, bismuth vanadate, Thénard's Blue, or organic coloured pigments, such as, for example, indigo, azo pigments, phthalocyanines or also Carmine Red, or elements such as, for example, yttrium or antimony. In a preferred embodiment, the outer layer on the substrate is a high-refractive-index metal oxide. This outer layer may additionally be on top of the above-mentioned layer packages or, in case of high-refractive-index supports, be a part of a layer package and can consist, for example, of TiO$_2$, titanium suboxides, Fe$_2$O$_3$, SnO$_2$, ZnO, ZrO$_2$, Ce$_2$O$_3$, CoO, Co$_3$O$_4$, V$_2$O$_5$, CR$_2$O$_3$ and/or mixtures thereof, such as, for example, ilmenite or pseudobrookite. TiO$_2$ is particularly preferred.

Said coated substrates may exhibit one or more angle-dependent interference colours. However, they may also produce just one absorption colour of the substrate or one absorption colour in addition to one or more angle-dependent interference colours.

The thickness of the metal oxide, metal oxide hydrate, metal suboxide, metal, metal fluoride, metal nitride or metal oxynitride layers or a mixture thereof is usually 3 to 500 nm and in the case of the metal oxide, metal oxide hydrate, metal suboxide, metal fluoride, metal nitride or metal oxynitride layers or a mixture thereof preferably 5 to 600 nm. The thickness of the metal layers is preferably 4 to 100 nm.

In the case of glass flakes as flake-form substrates, these are very particularly preferably coated with an $SiO_2$ layer. The $SiO_2$ coating protects the glass surface against chemical change, such as swelling, leaching-out of glass constituents or dissolution in the aggressive acidic coating solutions. During the calcination process in the production of these substrates, intimate bonding of the chemically related materials occurs in the case of the glass flakes at the interface between glass body and precipitated $SiO_2$. Owing to the high softening temperature, the precipitated $SiO_2$ sheath gives the substrates the requisite mechanical stability, even on calcination above 700° C. The adhesion of the coating(s) following the $SiO_2$ layers is also very good. The thickness of the $SiO_2$ layer on the glass flakes can be varied within broad ranges depending on the desired effect. The layer has thicknesses of 5-350 nm, preferably 5-150 nm. For control of lustre and colour strength, layer thicknesses of 30-100 nm are preferred. The $SiO_2$ layer may also be doped with carbon black particles, inorganic coloured pigments and/or metal particles so long as this doping is stable in air or under inert gas at temperatures >700° C. The proportion of dopant in the $SiO_2$ matrix is then 1-50% by weight, preferably 2-30% by weight, in particular 5-20% by weight. In a particularly preferred embodiment, a layer of a high-refractive-index metal oxide, in particular a $TiO_2$ layer, is applied to the $SiO_2$ layer.

In the case of spherical substrates based on $SiO_2$ (for example Mono-sphere® or Ronasphere®), these preferably have a coating of metal oxides, in particular of $TiO_2$ (for example Ronasphere® LDP).

Besides the above-mentioned flake-form, spherical or needle-shaped, coated or uncoated substrate or substrate mixture, the particles according to the invention have an anion-binding layer; in particular, the substrates are coated with the anion-binding layer. The anion-binding layer preferably comprises a layered double hydroxide. Layers of this type are also known as LDH layers.

The layered double hydroxide (LDH) is preferably a double hydroxide of the general formula

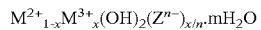
$$M^{2+}_{1-x}M^{3+}_x(OH)_2(Z^{n-})_{x/n} \cdot mH_2O$$

with 0.2<x<0.33, wherein
$M^{3+}$ is selected from $Al^{3+}, Cr^{3+}, Fe^{3+}, Ga^{3+}, In^{3+}, Y^{3+}, La^{3+}$ and/or $Ce^{3+}$ and
$M^{2+}$ is selected from $Ba^{2+}, Ca^{2+}, Cu^{2+}, Mg^{2+}, Sr^{2+}$ and/or $Zn^{2+}$,
$Z^{n-}$ denotes a counterion of the metal salts and/or an anion or anion mixture of the anion-forming organic functional active compounds, wherein n stands for the charge number of the anion.

m is a stoichiometric factor and indicates the content of water of crystallisation in the LDH. For the purposes of the present invention, m can be, for example, 1-12, but in addition also other values, which may be integers or non-integers.

Examples of the said double hydroxides are: $Mg_{0.67}Al_{0.33}(OH)_2(Z^{n-})_{0.33/n} \cdot mH_2O$ and $Mg_{0.67}Fe_{0.33}(OH)_2(Z^{n-})_{0.33/n} \cdot mH_2O$, $Zn_{0.67}Al_{0.33}(OH)_2(Z^{n-})_{0.33/n} \cdot mH_2O$ and $Zn_{0.67}Fe_{0.33}(OH)_2(Z^{n-})_{0.33/n} \cdot mH_2O$, $Ca_{0.67}Al_{0.33}(OH)_2(Z^{n-})_{0.33/n} \cdot mH_2O$ and $Ca_{0.67}Fe_{0.33}(OH)_2(Z^{n-})_{0.33/n} \cdot mH_2O$. $Ca_{0.67}Al_{0.33}(OH)_2(Z^{n-})_{0.33/n} \cdot mH_2O$, $Mg_{0.67}Al_{0.33}(Z^{n-})_{0.33/n} \cdot mH_2O$ and $Zn_{0.67}Al_{0.33}(OH)_2(Z^{n-})_{0.33/n} \cdot mH_2O$, which, in particular, have proven particularly advantageous.

Preferably, $M^{3+}=Al^{3+}$ or $Fe^{3+}$, and $M^{2+}=Mg^{2+}, Ca^{2+}$ or $Zn^{2+}$. Very particularly preferably, $M^{3+}=Al^{3+}$. The layer thickness of the anion-binding layer is 0.5-500 nm, in particular 1-300 nm.

The anion-binding layer comprises one or more anion-forming organic active compounds. The organic active compounds are, in particular, anionic or anion-forming medicament active compounds, food supplements, diagnostic substances and compounds and/or cosmetic active compounds, i.e. it is also possible for mixtures of the said active compounds to be present. In principle, there is no limitation with respect to the functional activity of the encapsulated active compounds, so long as they are anionic, preferably only anionic, or can be converted into anions. To this extent, it is possible to fix on the substrate organic substances or substance mixtures which function as active compounds in the sense of a pharmacological and/or skin-protecting and/or skin-care and/or skin-regenerating and/or antimicrobial and/or antifungicidal and/or cosmetic efficacy. In a preferred embodiment, these active compounds are in at least doubly anionically charged form or can be converted into at least doubly anionically charged molecules. Such molecules contain at least two anionic functional groups or functional groups which can be converted into an anion. These can be selected, for example, from the group of sulfonic acid (sulfonate) and/or carboxylic acid (carboxylate) and/or sulfuric acid monoester (sulfate) and/or phenol (phenoxide) and/or phosphoric acid mono- or diester (mono- or diphosphate) and/or phosphonates and/or enol (enolate) and/or anions of imidic acid and/or anions of dithiolic acids. The organic active compound thus contains one or more, in particular at least two, anion-forming phenoxide, enolate, carboxylate, sulfate, sulfonate, sulfinate, dithiolate, phosphate and/or phosphite structural units. In the case of these active compounds, skin contact/skin penetration which may be undesired (for example in the case of UV filters) is thus substantially avoided. This effect of immobilisation of the active compound, preservative or dye, in particular on use of at least doubly ionisable substances, strengthens the anion fixing in the case of the stabilisation function at pH >6 and suppresses undesired penetration via product safety increased in this way. It is thus possible to achieve virtually complete immobilisation at pH >6. However, it is also possible to establish controlled release of the active compounds, which results in better dosage of the active compounds, at pH <6.

Suitable anion-forming medicament active compounds are, for example:
1) Sedative medicaments: for example those of the barbituric acid derivatives, such as, for example, sodium amobarbital (CAS: 64-43-7)
2) Inflammation-inhibiting antirheumatics: for example those of the acetic acid derivatives, such as, for example, indomethacin (CAS: 53-86-1), acemetacin (CAS: 53164-05-9), tolmetin (CAS: 26171-23-3), diclofenac (CAS: 15307-86-5), lonozolac (CAS: 53808-88-1), and/or those of the propionic acid derivatives, such as, for example, ibuprofen (CAS: 15687-27-1), fenoprofen (CAS: 31879-05-7), sodium naproxen (CAS: 26159-34-2), ketoprofen (CAS: 22071-15-4)
3) Antiarteriosclerosis B vitamins: for example carnitin (CAS: 461-06-3), aluminium nicotinic acid (CAS: 1976-28-9), biotin (CAS: 58-85-5), calcium pantothenate (CAS: 137-08-6), aminobenzoic acid (CAS: 150-13-0)
4) Antiarrythmic, anticonvulsant non-steroids, such as, for example, voltaren/diclofenac (CAS: 15307-86-5)

5) Antiarrythmic, beta-sympatholytic substances from classes I, II, III and IV, such as, for example, bometolol (CAS: 65008-93-7) and BW-A-575-C (CAS: 103221-88-1)
6) β-Lactam antibiotics: for example those of the penam, crabapenem, oxapenam, cephem, oxacephem and monocyclic β-lactams, such as, for example, carbenicillin (CAS: 4697-36-3), amoxillin (CAS: 26787-78-0), cefoxitin (CAS: 35607-66-0) and ampicillin (CAS: 69-53-4)
7) Antibiotics from the family of the penicillins, aminopenicillins, acylamino-penicillins, carboxypenicillins and cephalosporins, such as, for example, tazobactam (CAS: 89786-04-9), cloxacillin sulfone (CAS: 76788-83-5), sulbactam (CAS: 68373-14-8)
8) Antibiotics from the family of the tetracyclins, such as, for example, glycinmethyltetracyclin (CAS: 751-98-4), lymecyclin (CAS: 992-21-2), calcium chlorotetracyclin (CAS: 57122-99-3), apicyclin (CAS: 15599-51-6)
9) Anticoagulants and clotting factor synthesis inhibitors from the family of the coumarol derivatives, such as, for example, warfarin (CAS: 5543-58-8), acenocoumarol (CAS: 152-72-7), 6-hydroxywarfarin (CAS: 17834-02-5), 3-hydroxywarfarin (CAS: 30992-81-5), coumachlorine (CAS: 81-82-3), 4-hydroxywarfarin (CAS: 63740-78-3)
10) Inflammation-inhibiting prostaglandin antagonists of the diphenylamine derivatives, such as, for example, clofenamic acid (CAS: 4295-55-0), aluminium lufenamate (CAS: 16449-54-0), sodium lobenzarit (CAS: 64808-48-6), flutiazin (CAS: 7220-56-6), araprofen (CAS: 15250-13-2)
11) Antiseptic agents and antidiabetic agents from the family of the phenylsulfonamides, such as, for example, aristoplomb (CAS: 60662-80-8), acrotiazol (CAS: 60595-59-7), BA-32641 (CAS: 92569-06-7), alfasol (CAS: 38114-83-9), carboxytolbutamide (CAS: 2224-10-4)
12) Inflammation inhibitors, analgesics, collagenase inhibitors and keratolytic substances, such as, for example, salicylic acid (CAS: 69-72-7)
13) Anticonvulsants, for example those of the valproate salts, such as, for example, calcium valproate (CAS: 33433-82-8), sodium valproate (CAS: 1069-66-5), semisodium valproate (CAS: 76584-70-8)
14) Antiasthmatics and antianaphylactics, for example those of the xanthin derivatives, such as, for example, acefyllin (CAS: 652-37-9), sodium ablukast (CAS: 96565-55-8), amlexanox (CAS: 68302-57-8), AH-7725 (CAS: 68302-57-8), calcium nedocromil (CAS: 101626-68-0)
15) Cytostatic agents and immunosuppressants, for example those of the azathioprin derivatives, such as, for example, sodium azathioprin (CAS: 55774-33-9), tiamiprin (CAS: 5581-52-2), metazathioprin (CAS: 97746-12-8)
16) Corticosteroids and progestogens, for example those of the prostaglandin derivatives, such as, for example, sodium methylprednisolone succinate (CAS: 2375-03-3), sodium betamethasone phosphate (CAS: 151-73-5)
17) Virucides, for example those of the guanosine derivatives, for example 2'-guanosine monophosphate (CAS: 130-50-7), 3'-guanosine monophosphate (CAS: 82570-66-9), aciclovir phosphate (CAS: 66341-16-0), 2'-cycloguanosine monophosphate NOR (CAS: 91516-85-7)
18) Thyroid hormones and antiarteriosclerotic agents, for example those of the diphenyl ether derivatives, such as, for example, detrothyronine (CAS: 5714-08-9), sodium levothyroxine (CAS: 55-03-8), sodium dextrothyroxine (CAS: 137-53-1)
19) Analgesics, inflammation inhibitors, antipyretics, for example those of the oxicam derivatives, such as, for example, meloxicam (CAS: 71125-38-7), isoxicam (CAS: 34552-84-6), piroxicam olamine (CAS: 85056-47-9), piroxicam phosphate (CAS: 82801-42-1), and/or those of the pyrazole derivatives, such as, for example, magnesium metamizol (CAS: 6150-97-6) and dibupyron (CAS: 1046-17-9), and/or those of the pyrazolidine derivatives, such as, for example, anthradione (CAS: 19854-90-1) and sulfodethamedione (CAS: 53039-87-5)
20) Chelating agents, such as, for example, HBED (CAS: 35998-29-9), calteridol (CAS: 132722-73-7), cadystin-A (CAS: 86220-45-3), sodium ditiocarb (CAS: 148-18-5), mugineic acid (CAS: 69199-37-7), CDTA (CAS: 13291-61-7), calcium pentetate (CAS: 2531-75-1)
21) Protozoocides, for example those of the artelinate derivatives, such as, for example, artesunate (CAS: 88495-63-0)
22) Prostaglandins for ulcer therapy, such as, for example, carbacyclin (CAS: 69552-46-1), ataprost (CAS: 83997-19-7), alfaprostol (CAS: 74176-31-1), sodium beraprost (CAS: 88475-69-8), AY-16809 (CAS: 21269-28-3), alpha-PGF1 (CAS: 745-62-0).

These examples are intended to explain the possibilities by way of example without restricting the choice.

Suitable anion-forming food supplements or cosmetic active compounds or diagnostic active compounds are, for example, the bioflavonoids listed below. In addition, all amino acids, such as, for example, glutamic acid and aspartic acid, furthermore amino acids having a betaine structure, such as, for example, ectoin, hydroxyectoin or trimethylglycine, are also suitable for this purpose. Anion-forming vitamins and vitamin derivatives, in particular phosphates, are likewise suitable in accordance with the present invention. Mention may be made here by way of example of vitamin C and vitamin C phosphate. It is furthermore possible to use: lipoic acids, anions of saturated or unsaturated fatty acids, retinoic acid, tocopherols ($\alpha$, $\beta$, $\gamma$, $\delta$), vitamin B1 (for example thiamine pyrophosphate), vitamin B2, vitamin B6 (pyridoxine, pyridoxal), nicotinic acid, pantothenic acid, biotin, folic acid, vitamin B12 (cyanocobalamine), nucleotides and nucleosides or derivatives thereof, such as, for example, nicotinamide adenine dinucleotide (NAD or $NADH_2$), adenosine triphosphate (ATP), adenosine monophosphate (AMP), adenosine diphosphate (ADP), 5'-inosine monophosphate (IMP), 5'-guanosine monophosphate (GMP), and creatine, creatine phosphate and creatinine.

Furthermore, DNA and/or RNA building blocks and DNA and/or RNA fragments or moieties are suitable.

Organic active compounds having, in particular, an antioxidative property are, in particular, dicarboxylic acids (oxalic acid, succinic acid) and hydroxy-carboxylic acids (lactic acid, malic acid, tartaric acid and citric acid).

Suitable anion-forming diagnostic substances and compounds are, for example:

X-ray contrast agents, such as, for example, iocetaminic acid (CAS: 16034-77-8), iodocetylic acid (CAS: 54510-20-2), meglumin acetrizoate (CAS: 22154-43-4), iodohippurinic acid (CAS: 147-58-0), sodium bunamiodate (CAS: 1923-76-8), acetrizoic acid (CAS: 85-36-9), but also diagnostic agents for other applications, such as, for example, dinitrochlorobenzene (CAS: 97-00-7), gluceptinic acid (CAS: 87-74-1), sodium indigotin disulfonate (CAS: 860-22-0), iocanlidinic acid (CAS: 74855-17-7), butedroninic acid (CAS: 51395-42-7), wofazurin (CAS: 7488-76-8), upenazim (CAS: 95268-62-5), Vert-Sulfo-J (CAS: 519-76-6), silver fluorescein (CAS: 25931-86-6), pankensan (CAS: 38219-60-2), succimer (CAS: 304-55-2).

These examples are merely intended to explain by way of example the possibilities for bound anionic food supplements or cosmetic active compounds or diagnostic substances, but without restricting the choice.

The cosmetic active compounds are, in particular, care and protective active compounds. Examples of protective active compounds are UV filters, substances having an antimicrobial or antifungicidal action or also preservatives.

The functional active compound is preferably selected from the class of the UV filters. In the case of UV filters as functional active compounds, complete immobilisation of the UV filters is preferred. In this way, possible skin contact of the UV filter, which is frequently undesired, is avoided. Furthermore, choice of corresponding UV filters as active compounds with correspondingly selected substrates (for example ZnO) enables the provision of a broad-band UV filter, which offers a broad absorption spectrum and thus improved protection owing to the different absorption properties of active compound and substrate.

Suitable anion-forming or anionic UV filters which absorb ultraviolet light radiation may be selected from p-aminobenzimidazole-5-sulfonates, 3-imidazol-4-ylacrylates, salicylates, p-methoxycinnamates, 2-ethylhexyl-2-cyano-3,3-diphenylacrylates, 3,3,5-trimethylcyclohexyl-2-acetamidobenzoates, p-aminobenzoates, cinnamates, 3,4-dimethoxyphenylglyoxylates, (2-oxoborn-3-ylidene)-p-xylene-2-sulfonates, (2-oxoborn-3-ylidene)toluene-4-sulfonates, cyano-4-methoxycinnamates and 2-phenylbenzimidazole-5-sulfonates.

These anions, if they are in the free state, are known for absorbing in the wavelength range from 290 to 400 nm. All representatives are regarded as compatible materials for sunscreen substances.

Fixing in the LDH layer enables the absorption profile of known UV filters to be retained or alternatively shifted in a specific manner. It is thus ultimately also possible to match the UV filter properties of the anion specifically to those of the substrate. It is particularly interesting and thus an embodiment of the present invention which is preferred in accordance with the invention to combine in this connection the possibility of UV-A and UV-B filter properties with one another in a stable manner in a single product.

A further group of organic materials which is suitable for the purposes according to the invention is that which has a weakly acidic functionality through inclusion of a phenolic proton or another weakly acidic proton in the molecule. It has been found as part of the present invention that this proton can be removed with formation of an anion which can be introduced into a layered double hydroxide. Anions derived from compounds of this type can have absorption spectra which differ significantly from the parent compound, but these anions, after mixing into a layered double hydroxide, exhibit characteristic light absorption between 290 and 400 nm (UV-A region). In a preferred embodiment according to the invention, an advantage arises from the fact that these anions, when mixed into layered double hydroxides, exhibit such spectra, so that increased UV-A protection arises compared with that obtained on use of the parent compounds in the absence of the layered double hydroxide. An important group of phenol compounds of this type comprises hydroxylated benzophenone derivatives. Suitable diketone compounds (for example dibenzoylmethanes, such as, for example, Eusolexe ® 9020), which are in their acidic enol form, may likewise be encapsulated. Examples of compounds from which anions used in the preferred embodiment according to the invention are derived include the following materials, but are not restricted thereto:

| CTFA name | Chemical name |
|---|---|
| Benzophenone-1 | 2,4-dihydroxybenzophenone |
| Benzophenone-2 | 2,2',4,4'-tetrahydroxybenzophenone |
| Benzophenone-3 | 2-hydroxy-4-methoxybenzophenone |
| Benzophenone-4 | 2-hydroxy-4-methoxybenzophenone-5-sulfonic acid |
| Benzophenone-5 | 2-hydroxy-4-methoxybenzophenone-5-sulfonic acid monosodium salt |
| Benzophenone-6 | 2,2'-dihydroxy-4,4'-dimethoxybenzophenone |
| Benzophenone-7 | 5-chloro-2-hydroxybenzophenone |
| Benzophenone-8 | 2,2'-dihydroxy-4-methoxybenzophenone |
| Benzophenone-9 | 2,2'-dihydroxy-4,4'-dimethoxybenzo-phenone-3,3'-disulfonic acid disodium salt |
| Benzophenone-10 | 2-hydroxy-4-methoxy-4'-methylbenzophenone |
| Benzophenone-12 | 2-hydroxy-4-octoxybenzophenone |
| Homosalate | homomenthyl salicylate |
| Octyl salicylate | 2-ethylhexyl salicylate |

A further compound which is able to provide interlayer anions is butyl-methoxydibenzoylmethane, obtainable as PARSOL 1789 from Givaudan Corp.

Likewise encapsulated in this form according to the invention are anionic species derived from pongomol, a substituted 1,3-diketone whose systematic name is 1-(4-methoxy-5-benzofuranyl)-3-phenyl-1,3-propanedione. It has an ultraviolet absorption band within the range from 250 to 500 nm and an absorbance coefficient of 5000 to 70,000. This diketone is described more precisely in U.S. Pat. No. 5,152,983, the disclosure content of which is hereby incorporated into the description.

Of these substances, both benzophenone-4 and also benzophenone-9 have a strongly acidic functionality, provided by a sulfonate group, and a weakly acidic functionality, provided by the phenolic proton. For these materials (and for benzophenone-5, namely the monosodium salt of benzophenone-4), polyanionic forms of the substance can be prepared and introduced into the hydroxide fixing layer. For example, benzophenone-4 can be fixed on the substrate both as the monoanion and as the dianion. Both monoanionic and dianionic forms of this material and any desired combinations thereof which are introduced into the layered double hydroxides may be suitable for sunscreens and are regarded as lying within the scope of protection of the invention.

The UV filters are particularly preferably selected from: phenylbenzimidazoliumsulfonic acid (CAS 27503-81-7; trade name Eusolex 232), benzophenone-4 (CAS 4065-45-6; trade name Uvinul-MS-40 (BASF)), benzylidenecamphorsulfonic acid (CAS 56039-58-8; trade name Mexoryl SL (Chimex/Loreal)), terephthalidenedicamphorsulfonic acid (CAS 90457-82-2; trade name Mexoryl SX (Chimex, Loreal)), disodium phenyldibenzimidazoliumtetrasulfonate (CAS 180898-37-7; trade name Neo Heliopan AP (Symrise)).

Suitable anion-forming preservatives are benzoic acid, salicylic acid, p-hydroxybenzoic acid, p-hydroxybenzoic acid esters (PHB esters), sorbic acid, propionic acid, acetic acid, sulfites, diethyl dicarbonate, dimethyl di-carbonate, nitrite, nitrate, anion-forming antibiotics and o-phenylphenol. Suitable anion-forming active compounds are likewise bioflavonoids which, owing to their basic structure, can be classified in the groups of the chalcones, aurones, flavanones, flavan-3-ols (catechins), flavones, isoflavones, flavan-3,4-diols (leukoanthocyanidines), flavonols (3-hydroxy-flaven-4-one) or flavanonols.

The following flavonoids should be mentioned by way of example: 5-hydroxy-7,4'-dimethoxyflavone 8-sulfate, 7,8-dihydroxyflavone, luteolin (flavones); catechin, epicatechin, epigallocatechin gallate (EGCG, TEA-VIGO® DSM) (flavan-3-ols or flavan-3-ol derivatives); kaempferol (flavonol); taxifolin (flavanonol).

Preferred flavonoids are derived from the groups of the flavonols, flavonol o-glycosides or flavonol o-glycoside-containing extracts. Flavonoids usually occur as soluble glycosides in the cell sap of plants. The preferred flavonoids also include aglycones (sugar-free structures) and aglycone conjugates. Possible aglycone conjugates are hydroxyl derivatives, wherein all or some of the hydroxyl groups are alkylated, methylated, glycylated, sulfated or esterified. Besides hydroxyl derivatives, C derivatives are also suitable as aglycone conjugates.

For the group of the flavonols, particular preference is given to the aglycone quercetin. In the group of the flavonol o-glycosides, the flavonol 3-glycosides, such as rutin, α-glucosylrutin, tiliroside, isoquercetin, rutin sulfate, trishydroxyethylrutin (troxerutin) and the sulfates and phosphates thereof, are particularly preferred. The term "rutin sulfate" encompasses mono-, di-, tri-, tetra- and polysulfates of rutin or mixtures of these rutin sulfates. The term "troxerutin" encompasses mono-, di-, tri-, tetra- and polyethoxylates of rutin or mixtures of these rutin ethoxylates. Flavonol 7- and 8-glycosides can also be used.

The substance classes described should only be regarded as illustrative and are merely intended to explain the present invention without limiting it. The various active compounds can of course be combined with one another, i.e. mixtures of a plurality of functional active compounds can be fixed on the substrate.

The amount of active compound thus fixed is between 0.001 and 50% by weight, based on the pigment as a whole. Preferably, between 0.5 and 20.0% by weight, in particular between 1.0 and 10.0% by weight, are fixed.

In a particularly preferred embodiment of the present invention, the anion-binding layer, besides the active compound, additionally comprises anion-forming organic, inorganic and/or organometallic colorants. This gives rise to multifunctional particles which, besides the functional action of the active compound, additionally exhibit a colour effect. In this way, two properties which are independent of one another are combined with one another. This has the advantage for the user that functional action and colour effect no longer have to be introduced into an application system via components to be added separately, but instead this can be carried out by addition of only one component. This simplifies the preparation of formulations and increases the variability for the applications. By simultaneous addition of a plurality of functions to the formulation in a single working step, savings can additionally be achieved by the customer via the shorter formulation time. This is augmented by the fact that the organic active compounds/colorants or mixtures thereof are already in a type of predispersed state due to the fixing on the substrate, since the unfixed organic active compounds/colorants are, as is known, frequently difficult to disperse. Due to the particles according to the invention, by contrast, this time-consuming and high-energy dispersal step is superfluous or only occurs in very greatly shortened form.

Particularly intense colour impressions are achieved if the interference colour of the substrate employed corresponds to the absorptive colour of the colorant. If the interference colour of the substrate differs from the absorptive colour of the colorant, attractive multicolour effects are achieved, which are then combined with the activity of the functional active compound.

Colorants of this type can be: anions derived from organic dyes or pigments or from dye or pigment precursors, or inorganic or organic anions or free-radical anions or coloured heteropolyanions, or a mixture of the above-mentioned colorants.

Colorants which can be employed for non-cosmetic applications are in principle all anionic or anion-forming dyes. Suitable here are, in particular, C.I. acid dyes, such as, for example: C.I. Acid Yellow 13, C.I. Acid Yellow 17, C.I. Acid Yellow 23, C.I. Acid Yellow 25, C.I. Acid Yellow 36, C.I. Acid Yellow 38, C.I. Acid Yellow 42, C.I. Acid Yellow 44, C.I. Acid Yellow 56, C.I. Acid Yellow 65, C.I. Acid Yellow 76, C.I. Acid Yellow 127, C.I. Acid Orange 7, C.I. Acid Orange 10, C.I. Acid Orange 19, C.I. Acid Orange 65, C.I. Acid Orange 67, C.I. Acid Red 1, C.I. Acid Red 13, C.I. Acid Red 14, C.I. Acid Red 32, C.I. Acid Red 37, C.I. Acid Red 38, C.I. Acid Red 42, C.I. Acid Red 88, C.I. Acid Red 119, C.I. Acid Red 131, C.I. Acid Red 138, C.I. Acid Red 154, C.I. Acid Red 249, C.I. Acid Red 299, C.I. Acid Violet 14, C.I. Acid Violet 42, C.I. Acid Violet 43, C.I. Acid Blue 25, C.I. Acid Blue 40, C.I. Acid Blue 43, C.I. Acid Blue 62, C.I. Acid Blue 92, C.I. Acid Blue 113, C.I. Acid Blue 117, C.I. Acid Blue 129, C.I. Acid Green 1, C.I. Acid Green 25, C.I. Acid Green 41, C.I. Acid Black 1, C.I. Acid Black 24, C.I. Acid Black 26, C.I. Acid Black 48, C.I. Acid Black 210, C.I. Acid Black 234, C.I. Acid Brown 14, C.I. Acid Brown 20.

In addition, C.I. reactive dyes are also suitable, such as, for example: C.I. Reactive Yellow 4, C.I. Reactive Yellow 17, C.I. Reactive Orange 1, C.I. Reactive Red 8, C.I. Reactive Red 12, C.I. Reactive Red 23, C.I. Reactive Blue 15, C.I. Reactive Blue 19, C.I. Reactive Blue 216, C.I. Reactive Black 5, C.I. Reactive Black 8, C.I. Reactive Black 31.

Also suitable are C.I. direct dyes, such as, for example: C.I. Direct Yellow 12, C.I. Direct Yellow 27, C.I. Direct Yellow 29, C.I. Direct Yellow 50, C.I. Direct Yellow 86, C.I. Direct Orange 26, C.I. Direct Red 23, C.I. Direct Red 75, C.I. Direct Red 76, C.I. Direct Red 79, C.I. Direct Red 80, C.I. Direct Red 81, C.I. Direct Red 250, C.I. Direct Blue 78, C.I. Direct Blue 86, C.I. Direct Blue 93, C.I. Direct Blue 106, C.I. Direct Green 26, C.I. Direct Black 19, C.I. Direct Black 22, C.I. Direct Black 51, C.I. Direct Black 150, C.I. Direct Black 151, C.I. Direct Black 166, C.I. Direct Black 168.

Finally, it is also possible to employ C.I. mordant dyes, such as, for example: C.I. Mordant Yellow 1, C.I. Mordant Yellow 5, C.I. Mordant Yellow 30, C.I. Mordant Red 7, C.I. Mordant Red 19, C.I. Mordant Red 30, C.I. Mordant Blue 7, C.I. Mordant Blue 13, C.I. Mordant Black 3, C.I. Mordant Black 9, C.I. Mordant Black 11, C.I. Mordant Brown 33, C.I. Mordant Brown 48, but also C.I. Solubilised Sulphur Red 11, and fluorescent dyes, such as, for example: C.I. Basic Yellow 40, C.I. Basic Red 12, C.I. Solvent Yellow 94.

Preference is given to the use of the anions of organic dyes and pigments or precursors and mixtures thereof which are approved in cosmetic applications. Examples are: FD&C Yellow 5 (tartrazine), FD&C Yellow 6 (Sunset Yellow FCF), FD&C Yellow 10, FD&C Red 3 (erythrosine), FD&C Red 6 (Litholrubin B), FD&C Red 7 (Litholrubin BN), FD&C Red 21, FD&C Red 27, FD&C Red 28 (Floxine B), FD&C Red 33, C.I. Natural Red 33, FD&C Red 36, FD&C Red 40, Carmine, FD&C Blue 1 (Brilliant Blue FCF), C.I. Natural Green 3 (E141), FD&C Blue, FD&C Black 1 (Brilliant Black).

It is, in particular, also possible to fix mixtures of at least two colorant anions above the anion-binding layer on the substrate. This gives rise to innumerable colour variants. Likewise, no restrictions at all are placed on the percentage composition of the colorant mixtures.

The colorants described should only be regarded as illustrative and are merely intended to explain the present invention without limiting it. The various substrates can of course also be combined with other anionic/lanion-forming organic or inorganic colorants.

The proportion of the anion-forming organic, inorganic and/or organometallic colorants or mixtures thereof is 0.01 to 30% by weight, based on the pigment as a whole, in particular 0.5 to 10% by weight.

In a particularly preferred and explained embodiment of the present invention, the anion-binding layer consisting of $Ca_{0.67}Fe_{0.33}(OH)_2(Z^{n-})_{0.33/n} \cdot mH_2O$ comprises a UV filter and/or skin-active substances. The composite has been precipitated onto a flake-form interference pigment. Multifunctional particles are thus obtained which are particularly suitable for use as skin-correctors in cosmetic applications. The interference colour of the substrate and the skin-coloured absorption colour of the anion-binding layer produce a directly perceptible optical correction of coloured skin inhomogeneities, and the substances bound in the composite ensure an advantageous additional effect which not only optically, but instead actively suppresses or at least reduces precisely these skin discolorations.

In a further embodiment of the present invention, a stabilising inorganic and/or organic coating has additionally been applied to the particles. This post-coating increases, depending on the area of application, the light, water and weather stability. The bleeding stability of the product is also further increased. Examples of coatings of this type are given, for example, in DE 22 15 191, DE 31 51 354, DE 33 34 598, EP 0 632 109, U.S. Pat. No. 5,759,255, DE 43 17 019, DE 39 29 423, DE 32 35 017, EP 0 492 223, EP 0 342 533, EP 0 268 918, EP 0 141 174, EP 0 764 191, WO 98/13426, EP 0 090 259, EP 0 634 459, WO 99/57204, WO 96/32446, WO 99/57204, U.S. Pat. No. 5,571,851, WO 01/92425 or EP 0 465 805, the disclosure content of which is hereby incorporated by way of reference. Suitable inorganic materials for the post-coating are the oxides and/or oxide hydrates of Al, Si, Zr, Ce, Zn, Fe and/or mixtures thereof, preferably the oxides and/or oxide hydrates of Al, Ce, Zn, Zr and/or Si. The said layers may be in the form of individual layers of the respective oxides and/or oxide hydrates, but also in the form of mixed layers. In addition, mixtures of oxides with sulfates, phosphates and/or borates can also be employed in addition to the oxides deposited alone. Examples of sulfates are $ZnSO_4$ and $CaSO_4$, examples of phosphates are $AlPO_4$ and $CePO_4$ and an example of borates is $AlBO_4$.

Layers of these materials are distinguished by high transparency, zero or only slight inherent colour and high lustre, meaning that the colouristic properties of the particles are not modified. Overall, the respective proportions for the additional stabilising coating should be selected so that the optical properties of the particles according to the invention are not significantly affected.

The organic coating optionally applied acts as coupling reagent and can consist of organosilanes, organoaluminates, organotitanates and/or organozirconates of the general formula

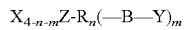

where X=OH, halogen, alkoxy or aryloxy
Z=Si, Al, Ti or Zr
R=alkyl, phenyl or hydrogen
B=organic, at least bifunctional group (alkylene or alkyleneoxyalkylene)
Y=amino, substituted amino, hydroxyl, hydroxyalkyl, siloxane, acetoxy, isocyanate, vinyl, acryloyl, epoxide, epoxypropyloxy, imidazole or ureido group
n and m=0, 1, 2 or 3, where n+m≦3.

The coupling reagents consist of an anchor group ($X_{4-n-m}Z$), which binds to the surface, at least one hydrophobic group (R,B) and one or more functional groups (Y). The coupling reagents are preferably compounds where Z=Si. The anchor group preferably consists of alkoxysilanes, which can be converted by hydrolytic reaction conditions into corresponding hydroxyl groups. The latter are able to bind to the surface of the particles and effect the anchoring via oxygen bridges. In addition, it is also possible to employ mixtures of different coupling reagents, which can be applied as a mixture or individually.

The organic coating can be matched to the use medium through the choice of suitable functional groups. In addition, additional bonds can be formed between pigment and medium via the coupling reagent through reaction of the functional groups with corresponding functionalities in the application media. In a particular embodiment, the surface of the pigments according to the invention is modified with a combination of organic functionalities which is matched to the use medium. Also suitable for this purpose is the use of mixtures of different coupling reagents within the organic coating. The hydrophobicity of the pigment surface can be adapted by integration of alkyl-containing coupling reagents, such as, for example, alkylsilanes. Besides the organosilanes, the use of hydrolysates thereof and of homogeneous and heterogeneous oligomers and/or polymers, which can likewise be employed alone or in combination with silanes, zirconates, aluminates, zirconaluminates and/or carboxyzirconaluminates as organic coating, is also preferred. Particular preference is given to an organic coating comprising mixtures of different coupling reagents, in particular with functional groups Y which are different from one another, which ensures a particularly wide range of applications.

Examples of organosilanes are propyltrimethoxysilane, propyltriethoxysilane, isobutyltrimethoxysilane, n-octyltrimethoxysilane, i-octyltrimethoxysilane, n-octyltriethoxysilane, n-decyltrimethoxysilane, dodecyltrimethoxysilane, hexadecyltrimethoxysilane, vinyltrimethoxysilane, preferably n-octyltrimethoxysilane and n-octyltriethoxysilane. Suitable oligomeric, alcohol-free organosilane hydrolysates are, inter alia, the products marketed by Sivento under the trade name "Dynasylan®" such as, for example, Dynasylan HS 2926, Dynasylan HS 2909, Dynasylan HS 2907, Dynasylan HS 2781, Dynasylan HS 2776, Dynasylan HS 2627. In addition, oligomeric vinylsilane and aminosilane hydrolysate are suitable as organic coating. Functionalised organosilanes are, for example, 3-aminopropyltrimethoxysilane, 3-methacryloxytrimethoxysilane, 3-glycidyloxypropyltrimethoxysilane, beta-(3,4-epoxycyclohexyl)ethyltrimethoxysilane, gamma-isocyanatopropyltrimethoxysilane, 1,3-bis(3-glycidoxypropyl)-1,1,3,3-tetramethyldisiloxane, ureidopropyltriethoxysilane, preferably 3-aminopropyltrimethoxysilane, 3-methacryloxytrimethoxysilane, 3-glycidyloxypropyltrimethoxysilane, beta-(3,4-epoxycyclohexyl)ethyltrimethoxysilane, gamma-isocyanatopropyltrimethoxysilane. Examples of polymeric silane systems are described in WO 98/13426 and are marketed, for example, by Sivento under the trade name Hydrosil®.

The amount of organic coating is between 0.2 and 5% by weight, based on the pigment, preferably 0.5 to 2% by weight.

The present invention furthermore relates to processes for the production of the particles according to the invention, in which a suspension of substrate(s), metal cation salts, active-compound or colorant salts or mixtures of these salts (abbreviated to "active-compound salt" below), and lyes and/or urea in a solvent or solvent mixture is stirred at a temperature of 50-120° C. so that the anion-binding layer forms on the substrate, wherein the anion-binding layer comprises anion-forming organic active compounds, and the product is subsequently separated off, washed, dried and optionally sieved.

In the simplest case, the substrate, the metal cation salts and active-compound salt(s) are initially introduced in a suspension together with lye and/or lye precursors and, in the case of layered double hydroxides, depending on the type of LDH and active-compound salt employed, stirred at a temperature of 10-120° C. for 2 to 48 hours. After the reaction suspension has been cooled, the product is filtered off with suction and washed with a suitable solvent until the filtrate running out is virtually free of active compound. The filter cake is subsequently dried at 50-180° C. and optionally sieved to the desired fineness.

In a further variant, a solution of the metal cation salts can be added to a suspension of substrate(s), active-compound salts and lyes and/or lye precursors. In the simplest case, this means that the substrate, lye and/or lye precursors and active-compound salt(s) are initially introduced in a suspension. A solution of the metal cation salts is subsequently added dropwise at room temperature. After completion of the addition, the reaction mixture is heated to 50-100° C. and stirred at this temperature for 2 to 48 hours, depending on the type of LDH and active compound. After the reaction suspension has been cooled, the product is filtered off with suction and washed with a suitable solvent until the filtrate running out is virtually free of active compound. The filter cake is subsequently dried at 50-180° C. and optionally sieved to the desired fineness.

Suitable lyes are aqueous solutions of NaOH, KOH or $NH_3$, but also lye precursors, such as, for example, urea, which only release the actual lye in the reaction medium, for example through hydrolysis. The pH during the reaction (which means the pH behaviour throughout the reaction) is usually in the range from 2 to 13, in particular from 3 to 11.

Suitable metal cations for the formation of the LDH layer are known from the literature. Suitable metal cation salts are in principle all soluble salts with $Al^{3+}$, $Cr^{3+}$, $Fe^{3+}$, $Ga^{3+}$, $In^{3+}$, $Y^{3+}$, $La^{3+}$, $Ce^{3+}$, $Ba^{2+}$, $Ca^{2+}$, $Cu^{2+}$, $Mg^{2+}$, $Sr^{2+}$ and/or $Zn^{2+}$ cations, from which the anion-binding layer consisting of a layered double hydroxide can be produced. In particular, the said metal cation salts are the corresponding halides, in particular chlorides, bromides or iodides. However, the sulfates and nitrates of the metal cations are also suitable. The corresponding chlorides and nitrates are very particularly preferably employed.

In an alternative, two-step variant of the production of the multifunctional particles according to the invention, a suspension of the substrate/Isubstrate mixture, metal cation salts and lyes and/or urea in a solvent or solvent mixture is stirred at a temperature of 10-120° C. so that the anion-binding layer consisting of a layered double hydroxide forms on the substrate, and the intermediate is then separated off, washed, dried at 50-300° C. and optionally sieved. This LDH-coated substrate is subsequently added to a solution of the anion-forming organic functional active compound with stirring. In this process variant, ion exchange occurs, where the anion $Z^{n-}$ of the anion-binding double hydroxide is replaced by the anion-forming active compound. After the reaction suspension has been cooled, the product is filtered off with suction and washed. The filter cake is dried at 40-70° C. The dry hybrid pigment can subsequently optionally be ground and/or sieved.

In the last-mentioned method, the metal salts employed should preferably be corresponding chlorides or nitrates since these two anions are exchanged the fastest in the subsequent step. This two-step method is also particularly suitable for temperature-sensitive active compounds since, compared with the other processes, the active compound is not subjected to high temperatures for an extended time during the synthesis and in addition the active-compound-containing end product can be dried at significantly lower temperature.

It has, in addition, also proven advantageous in this two-step synthesis variant to calcine the intermediate at temperatures of 300-600° C. with the anion-binding layer consisting of a layered double hydroxide formed on the substrate before addition to the solution of the anion-forming organic active compounds. Here, the LDH-coated substrate is firstly converted into an LDO-coated substrate by calcination at 300-600° C. The LDO ("layered double oxide") subsequently re-forms the LDH structure in aqueous or water-containing medium and facilitates easier and more complete intercalation.

In an alternative variant of the two-step process described above, it is also possible firstly to prepare a suspension of the LDH- or LDO-coated substrate, to which a solution of the active-compound anion is then added at 20-70° C. with stirring. The mixture can usually be stirred at this temperature for 2 to 48 h. When fixing of the active-compound anion is complete, the product is filtered off with suction and washed with a suitable solvent until the filtrate running out is virtually free of active compound. The filter cake is subsequently dried at 40-70° C. and optionally sieved to the desired fineness.

The above-mentioned processes are suitable both for the production of particles comprising active compounds and also for the preferred production of particles comprising a combination of active compounds and colorants. The colorants here may already be present from the beginning in a mixture with the active compounds or added subsequently. In particular, it is also possible firstly to produce a particle comprising colorant or active compound and subsequently to incorporate the respective other component into the anion-binding layer by means of ion exchange, as described above, in a further step.

In addition, an inorganic and/or organic coating can additionally be applied as outer layer in a process which is likewise in accordance with the invention. Examples of coating processes of this type are given, inter alia, in EP 0 632 109, U.S. Pat. No. 5,759,255, DE 43 17 019, DE 39 29 423, DE 32 35 017, EP 0 492 223, EP 0 342 533, EP 0 268 918, EP 0 141 174, EP 0 764 191, WO 98/13426 or EP 0 465 805. Examples of inorganic and/or organic coatings and the associated advantages have already been described above under synthesis of the pigments according to the invention. The process step of application of the organic coating can be carried out immediately after the other steps of the process according to the invention. The coupling reagents are applied in solution at temperatures above 60° C., preferably above 70° C. Suitable solvents are organic solvents, water or mixtures thereof, preferably water. The reaction time necessary for application of the organic coating is at least 5 minutes, it preferably taking place over a period of 10 to 90 minutes, but this can also be extended as desired. The pigment obtained is worked up and isolated by methods which are familiar to the person skilled in the art, for example by filtration, drying and sieving.

The particles according to the invention can be employed in a variety of applications. Accordingly, the present invention likewise relates to the use of the particles according to the invention in cosmetics, pharmaceuticals, formulations, paints, coatings, plastics, films, in security printing, in security features in documents and identity papers, for colouring seed, for colouring foods or in medicament coatings and for the preparation of pigment compositions and dry preparations.

In the case of cosmetics, the hybrid pigments according to the invention are particularly suitable for products and formulations in decorative and care cosmetics, such as, for example, ointments, creams, pastes, nail varnishes, colouring powders, lipsticks or eye shadows, soaps, toothpastes, self-tanning formulations, etc. The hybrid pigments according to the invention can of course also be combined in the formulations with cosmetic raw materials and assistants of all types. These include, inter alia, oils, fats, waxes, film formers, preservatives and assistants which generally determine the applicational properties, such as, for example, thickeners and rheological additives, such as, for example, bentonites, hectorites, silicon dioxide, Ca silicates, gelatine, high-molecular-weight carbohydrates and/or surface-active assistants, etc. Formulations comprising the hybrid pigments according to the invention may be of the lipophilic, hydrophilic or hydrophobic type. In the case of heterogeneous formulations having discrete aqueous and nonaqueous phases, the particles according to the invention may be present in each case in only one of the two phases or alternatively distributed over both phases.

The pH values of the aqueous formulations can be between 4 and 14, preferably between 5 and 11 and particularly preferably between 6 and 9. As already outlined, the pH in the formulation determines the function of the LDH fixing layer: at pH <6, the slow dissolution of the LDH gives rise to a controlled-release function. By contrast, if a pH >6 prevails in the formulation, the LDH is stable and thus serves as solid "container" for the bound anions. The use range or controlled-release function is of course significantly influenced by an optional post-coating already mentioned. Thus, stabilisation in a broader pH range by a post-coating may be accompanied by the partial or complete loss of the controlled-release function. The latter is, for example, preferably accomplished during the fixing of UV filters.

Organic UV filters are generally incorporated into cosmetic formulations in an amount of 0.5 to 10 per cent by weight, preferably 1-8%, and inorganic filters in an amount of 0.1 to 30%.

The concentrations of the hybrid pigments according to the invention in the formulation are unlimited. They may—depending on the application—be between 0.001 (rinse-off products, for example shower gels) and 99% (for example lustre-effect articles for particular applications). The hybrid pigments according to the invention may furthermore also be combined with cosmetic active compounds. Suitable active compounds are, for example, insect repellents, UV A/BC protection filters (for example OMC, B3, MBC), anti-ageing active compounds, vitamins and derivatives thereof (for example vitamin A, C, E etc.), self-tanning agents (for example DHA, erythrulose, inter alia) and further cosmetic active compounds, such as, for example bisabolol, LPO, ectoin, emblica, allantoin, bioflavanoids and derivatives thereof. In general, the particles according to the invention can also be combined with the substances/substance mixtures which are also bound to the substrate via the anion-binding layer. This makes available, for example, formulations in which an immediate action after application of the formulation (by non-bound active compounds) is accompanied by an additional delayed action (controlled release of LDH-bound active compounds) over an extended period.

The preparations according to the invention may in addition comprise further conventional skin-protecting or skin-care active compounds. These may in principle be any active compounds known to the person skilled in the art.

Particularly preferred active compounds are pyrimidinecarboxylic acids and/or aryl oximes.

Of the cosmetic applications, particular mention should be made of the use of ectoin and ectoin derivatives for the care of aged, dry or irritated skin.

Thus, European patent application EP-A-0 671 161 describes, in particular, that ectoin and hydroxyectoin are employed in cosmetic preparations, such as powders, soaps, surfactant-containing cleansing products, lipsticks, rouge, make-up, care creams and sunscreen preparations.

Application forms of the cosmetic formulations which may be mentioned are, for example: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower preparations. Any desired customary carriers, assistants and, if desired, further active compounds may be added to the preparation.

Ointments, pastes, creams and gels may comprise the customary carriers, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary carriers, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary carriers, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, maizegerm oil, olive oil, castor oil and sesame oil, glycerol fatty acid esters, polyethylene glycols and fatty acid esters of sorbitan, or mixtures of these substances.

Suspensions may comprise the customary carriers, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary carriers, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary carriers, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary carriers, such as synthetic oils, such as, for example, fatty acid esters, fatty alcohols, silicone oils, natural oils, such as vegetable oils and oily plant extracts, paraffin oils, lanolin oils, or mixtures of these substances.

The cosmetic preparations may exist in various forms. Thus, they can be, for example, a solution, a water-free preparation, an emulsion or microemulsion of the water-in-oil (W/O) or oil-in-water (O/W) type, a multiple emulsion, for example of the water-in-oil-in-water (W/O/N) type, a gel, a solid stick, an ointment or an aerosol. It is also advantageous to administer ectoins in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W, emulsions are obtainable in a conventional manner.

Further embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

Solid sticks consist of natural or synthetic waxes and oils, fatty alcohols, fatty acids, fatty acid esters, lanolin and other fatty substances.

If a preparation is formulated as an aerosol, the customary propellants, such as alkanes, fluoroalkanes and chlorofluoroalkanes, are generally used.

The cosmetic preparation may also be used to protect the hair against photochemical damage in order to prevent colour changes, bleaching or damage of a mechanical nature. In this case, a suitable formulation is in the form of a rinse-out shampoo, lotion, gel or emulsion, the preparation in question being applied before or after shampooing, before or after colouring or bleaching or before or after permanent waving. It is also possible to select a preparation in the form of a lotion or gel for styling or treating the hair, in the form of a lotion or gel for brushing or blow-waving, in the form of a hair lacquer, permanent waving composition, colorant or bleach for the hair.

The preparation having light-protection properties may comprise adjuvants, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

On use of the particles in paints and coatings, all areas of application known to the person skilled in the art are possible, such as, for example, powder coatings, automobile paints, printing inks for gravure, offset, screen or flexographic printing, and coatings in outdoor applications. The paints and coatings here can be, for example, radiation-curing, physically drying or chemically curing. A multiplicity of binders is suitable for the preparation of printing inks or liquid surface coatings, for example based on acrylates, methacrylates, polyesters, polyurethanes, nitrocellulose, ethylcellulose, polyamide, polyvinyl butyrate, phenolic resins, maleic resins, starch or polyvinyl alcohol, amino resins, alkyd resins, epoxy resins, polytetrafluoroethylene, polyvinylidene fluorides, polyvinyl chloride or mixtures thereof, in particular water-soluble grades. The surface coatings can be powder coatings or water- or solvent-based coatings, where the choice of the coating constituents is part of the general knowledge of the person skilled in the art. Common polymeric binders for powder coatings are, for example, polyesters, epoxides, polyurethanes, acrylates or mixtures thereof.

In addition, the particles according to the invention can be used in films and plastics, for example in agricultural sheeting, infrared-reflective foils and sheets, gift foils, plastic containers and mouldings for all applications known to the person skilled in the art. Suitable plastics for the incorporation of the particles according to the invention are all common plastics, for example thermosets or thermoplastics. The description of the possible applications and the plastics which can be employed, processing methods and additives are given, for example, in RD 472005 or in R. Glausch, M. Kieser, R. Maisch, G. Pfaff, J. Weitzel, Perlglanzpigmente [Pearlescent Pigments], Curt R. Vincentz Verlag, 1996, 83 ff., the disclosure content of which is also incorporated herein.

In addition, the particles according to the invention are also suitable for use in security printing and in security-relevant features for, for example, forgery-proof cards and identity papers, such as, for example, entry tickets, personal identity papers, banknotes, cheques and cheque cards, and for other forgery-proof documents. In the area of agriculture, the particles can be used for colouring seed and other starting materials, in addition in the food sector for pigmenting foods. The particles according to the invention can likewise be employed for pigmenting coatings in medicaments, such as, for example, tablets or dragees.

The particles according to the invention are likewise suitable in the above-mentioned areas of application for use in blends with organic dyes and/or pigments, such as, for example, transparent and opaque white, coloured and black pigments, and with flake-form iron oxides, organic pigments, holographic pigments, LCPs (liquid crystal polymers) and conventional transparent, coloured and black lustre pigments based on metal oxide-coated flakes based on mica, glass, $Al_2O_3$, $Fe_2O_3$, $SiO_2$, etc. Examples and embodiments of the above-mentioned materials and pigment structures are also given, for example, in Research Disclosures RD 471001 and RD 472005, the disclosure contents of which are incorporated herein by way of reference. The particles according to the invention can be mixed in any ratio with commercially available pigments and fillers.

Fillers which may be mentioned are, for example, natural and synthetic mica, nylon powder, pure or filled melamine resins, talc, glasses, kaolin, oxides or hydroxides of aluminium, magnesium, calcium, zinc, BiOCl, barium sulfate, calcium sulfate, calcium carbonate, magnesium carbonate, carbon, and physical or chemical combinations of these substances. There are no restrictions with respect to the particle shape of the filler. It can be, for example, flake-form, spherical or needle-shaped in accordance with requirements.

The particles according to the invention are furthermore suitable for the preparation of flowable pigment compositions and dry preparations comprising one or more particles according to the invention, binders and optionally one or more additives. Dry preparations are also taken to mean preparations which comprise 0 to 8% by weight, preferably 2 to 8% by weight, in particular 3 to 6% by weight, of water and/or a solvent or solvent mixture. The dry preparations are preferably in the form of pellets, granules, chips, sausages or briquettes and have particle sizes of 0.2-80 mm. The dry preparations are used, in particular, in the preparation of printing inks and in cosmetic formulations.

The present invention furthermore relates to cosmetics, pharmaceuticals, formulations, paints, coatings, plastics, films, documents and identity papers, seed, foods or medicament coatings and pigment compositions and dry preparations comprising particles according to the present invention.

The complete disclosure content of all patent applications, patents and publications mentioned above is incorporated into this application by way of reference.

The following examples are intended to explain the invention in greater detail, but without limiting it.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

EXAMPLES

Example 1

50 g of glass flakes (ECR glass; fraction: 10-100 µm, substrate thickness: 870 nm) are added to 300 ml of water and 150 ml of NaOH (0.5 M). After stirring for 30 min, 2.9 g of C.I. FD&C Red 6 "Unipure Red LC303" as dye and 2.9 g of Neo Heliopan AP as UV-A filter are added. 10.15 g of $MgCl_2 \times 6H_2O$, 6.05 g of $AlCl_3 \times 6H_2O$ and 20.95 g of urea are each dissolved in about 100 ml of water and likewise added. The mixture is stirred under reflux for 24 h. The suspension is allowed to cool, and the residue is filtered off with suction and washed with water. The residue is dried at 50° C., giving glittering particles having a bright-red colour which have an additional absorption band in the UV-A region due to the content of organic UV filter.

Example 2

50 g of a red interference pigment (ECR glass coated with about 4% by weight of $SiO_2$, about 1% by weight of $SnO_2$ and about 25% by weight of $TiO_2$; fraction: 10-100 µm, substrate thickness: 850 nm) are added to 190 ml of water and 310 ml of NaOH (0.5 M). After stirring for 30 min, 4 g of rutin sulfate (a specific bioflavonoid) are added as active compound. 10.15 g of $MgCl_2 \times 6H_2O$ are dissolved in about 150 ml of water, mixed with 9.3 g of $FeCl_3$ solution comprising 15% by weight of Fe and added over the course of one hour with stirring. The mixture is subsequently made up to a total volume of 750 ml with water. The mixture is stirred under reflux for 12 h. The suspension is allowed to cool, and the residue is filtered off with suction and washed with water until the filtrate running out is virtually free of active compound. The residue is dried at 60° C., giving a glittering pigment having a red interference colour which releases the antioxidative action of rutin sulfate at a pH <6 in the formulation.

Example 3 a) 50 g of Timiron® Splendid Red (a multilayered red interference pigment based on mica in the fraction 10-60 µm) are added to 190 ml of water and 310 ml of NaOH (0.5 M), and the mixture is stirred for 30 min. 7.34 g of $CaCl_2 \times 2H_2O$ and 6.05 g of $AlCl_3 \times 6H_2O$ are dissolved in about 200 ml of water and added over the course of one hour with stirring. The mixture is subsequently made up to a total volume of 750 ml with water. The mixture is stirred under reflux for 12 h. The suspension is allowed to cool, and the residue is filtered off with suction and washed with about two litres of water. The residue is firstly dried at 110° C. and subsequently calcined at 300-600° C.

b) 2.9 g of phenylbenzimidazoliumsulfonic acid (Eusolex® 232, a UV-B filter) are dissolved in 500 ml of water at pH=7.5-8.0. 25 g of intermediate from step a) are then added. The suspension is stirred for 12 hours, and the product is filtered off with suction, washed with water until UV filter is no longer detectable in the filtrate and subsequently dried at 50° C., giving a pigment having a weakly red interference colour which has an additional absorption band in the UV-B region due to the content of UV filter.

The preceding examples can be repeated with similar success by substituting the generically or specifically described reactants and/or operating conditions of this invention for those used in the preceding examples.

The entire disclosure[s] of all applications, patents and publications, cited herein and of corresponding German application No. 102006024289.0, filed May 24, 2006 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A particle comprising a substrate and coated thereon an anion-binding layer which comprises one or more anion-forming organic active compounds, wherein at least one of the one or more anion-forming organic active compounds is not an anionic or anion-forming dye, wherein one or more transparent, semitransparent and/or opaque layers of metal oxides, metal oxide hydrates, metal suboxides, metals, metal fluorides, metal nitrides, metal oxynitrides or a mixture thereof has been applied to the substrate beneath the anion-binding layer, or wherein the substrate is flake-form shaped and is selected from the group consisting of glass flakes, $SiO_2$ flakes $Al_2O_3$ flakes, BiOCl flakes, graphite flakes, synthetic and natural flake-form iron oxide and flake-form metals, and aluminium, titanium, bronze, steel and silver metal flakes, wherein the metal flakes are optionally passivated, or wherein the substrate is flake-form shaped and has a diameter of 5 to 200 µm, an average thickness of 0.05 to 10 µm, and an average aspect ratio of 5 to 750.

2. A particle according to claim 1, wherein the anion-binding layer comprises a layered double hydroxide.

3. A particle according to claim 1, wherein the substrate is flake-form, spherical, needle-shaped or irregularly shaped.

4. A particle according to claim 1, wherein the one or more organic active compounds contain one or more anion-forming phen-oxide, enolate, carboxylate, sulfate, sulfonate, sulfinate, dithiolate, phosphate and/or phosphite groups.

5. A particle according to claim 1, wherein the one or more organic active compounds contain at least two anion-forming phen-oxide, enolate, carboxylate, sulfate, sulfonate, sulfinate, dithiolate, phosphate and/or phosphite groups.

6. A particle according to claim 1, wherein one or more transparent, semitransparent and/or opaque layers of metal oxides, metal oxide hydrates, metal suboxides, metals, metal fluorides, metal nitrides, metal oxynitrides or a mixture thereof has been applied to the substrate beneath the anion-binding layer.

7. A particle according to claim 1, wherein the substrates are doped.

8. A particle according to claim 1, wherein the anion-binding layer comprises a double hydroxide of formula

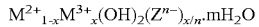

$M^{2+}_{1-x}M^{3+}_x(OH)_2(Z^{n-})_{x/n} \cdot mH_2O$ wherein $0.2 < x < 0.33$, $M^{3+}$ is $Al^{3+}$, $Cr^{3+}$, $Fe^{3+}$, $Ga^{3+}$, $In^{3+}$, $Y^{3+}$, $La^{3+}$ and/or $Ce^{3+}$ and $M^{2+}$ is $Ba^{2+}$, $Ca^{2+}$, $Cu^{2+}$, $Mg^{2+}$, $Sr^{2+}$ and/or $Zn^{2+}$, Z is a counterion of a metal salt and/or an anion or anion mixture of the anion-forming organic active compound, n stands for the charge number of the anion, and m is a stoichiometric factor and indicates a content of water of crystallization.

9. A particle according to claim 8, wherein $M^{3+}$ is $Al^{3+}$ or $Fe^{3+}$, and $M^{2+}$ is $Mg^{2+}$, $Ca^{2+}$ or $Zn^{2+}$.

10. A particle according to claim 1, wherein the layer thickness of the anion-binding layer is 0.5-500 nm.

11. A particle according to claim 1, wherein the proportion of the one or more anion-forming active compounds is 0.001 to 50% by weight, based on the particles as a whole.

12. A particle according to claim 1, wherein the anion-binding layer, besides the active compound, additionally comprises one or more anion-forming organic, inorganic and/or organometallic colorants.

13. A particle according to claim 12, wherein the proportion of the anion-forming organic, inorganic and/or organometallic colorants is 0.01 to 30% by weight, based on the particles as a whole.

14. A particle according to claim 1, wherein a stabilizing inorganic and/or organic coating has additionally been applied to the particle.

15. A particle according to claim 1, wherein the substrate is flake-form shaped and is selected from the group consisting of glass flakes, $SiO_2$ flakes, $Al_2O_3$ flakes, BiOCl flakes, graphite flakes, synthetic and natural flake-form iron oxide and flake-form metals, and aluminium, titanium, bronze, steel and silver metal flakes, wherein the metal flakes are optionally passivated.

16. A particle according to claim 1, wherein the substrate is flake-form shaped and has a diameter of 5 to 200 μm, an average thickness of 0.05 to 10 μm, and an average aspect ratio of 5 to 750.

17. A cosmetic composition, pharmaceutical composition, paint, coating, plastic composition or article, film, document or identity paper, seed, food, medicament coating, pigment composition or dry preparation comprising particles according to claim 1.

18. A process for preparing particles according to claim 1, comprising stirring a suspension of substrates, metal cation salt(s), anion-forming organic active-compound salt(s) and optionally colorant salt(s), and lyes and/or urea in a solvent or solvent mixture at a temperature of 50-120° C. so that an anion-binding layer forms on the substrate, and subsequently separating off, washing, drying and optionally sieving the resultant product.

19. A process according to claim 18, comprising adding a solution of metal cation salt(s) to a suspension of the substrates, anion-forming organic active-compound salt(s) and optionally colorant salt(s), and lyes and/or urea.

20. A process for preparing particles according to claim 1, comprising stirring a suspension of substrates, metal cation salt(s) and lyes and/or urea in a solvent or solvent mixture at a temperature of 50-120° C. so that an anion-binding layer forms on the substrate, then separating off, washing, drying and optionally sieving, the resultant product, which is subsequently added to a solution of one or more anion-forming organic active compounds and optionally anion-forming colorants with stirring.

21. A process according to claim 20, comprising calcining at a temperature of 300-600° C. with the anion-binding layer formed on the substrate before addition to the solution of the one or more anion-forming organic active compounds and optionally anion-forming colorants.

22. A method for stabilizing an active compound, comprising bringing the particle according to claim 1 to a pH of >6.

23. A method for releasing an active compound in a controlled manner, comprising bringing the particle according to claim 1 to a pH of <6.

* * * * *